United States Patent
Fullam (10) Patent No.: US 9,699,436 B2
(45) Date of Patent: Jul. 4, 2017

(54) DISPLAY WITH EYE-DISCOMFORT REDUCTION

(71) Applicant: Microsoft Technology Licensing, LLC, Redmond, WA (US)

(72) Inventor: Scott Fullam, Palo Alto, CA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 14/487,622

(22) Filed: Sep. 16, 2014

(65) Prior Publication Data

US 2016/0080720 A1 Mar. 17, 2016

(51) Int. Cl.
| | |
|---|---|
| H04N 13/00 | (2006.01) |
| G02B 27/01 | (2006.01) |
| G02B 27/00 | (2006.01) |
| G06F 3/01 | (2006.01) |
| H04N 13/04 | (2006.01) |
| A61B 3/00 | (2006.01) |

(Continued)

(52) U.S. Cl.
CPC ........... *H04N 13/0033* (2013.01); *A61B 3/00* (2013.01); *A61B 3/113* (2013.01); *A61B 3/14* (2013.01); *G02B 27/0093* (2013.01); *G02B 27/0101* (2013.01); *G06F 3/013* (2013.01); *H04N 13/0022* (2013.01); *H04N 13/044* (2013.01); *H04N 13/0484* (2013.01); *H04N 13/0497* (2013.01); *G02B 2027/014* (2013.01); *G02B 2027/0118* (2013.01); *G02B 2027/0134* (2013.01)

(58) Field of Classification Search
CPC .......... H04N 13/0033; H04N 13/0484; H04N 13/0022; H04N 13/0011; H04N 2013/0081; G02B 27/0101; G02B 27/0093; G02B 2027/014; G02B 2027/0118; G02B 2027/0134; G06F 3/013

See application file for complete search history.

(56) References Cited

U.S. PATENT DOCUMENTS

| | | |
|---|---|---|
| 6,690,351 B1 | 2/2004 | Wong |
| 7,522,344 B1 | 4/2009 | Curatu et al. |
| 7,744,216 B1 | 6/2010 | Uhlhorn |

(Continued)

FOREIGN PATENT DOCUMENTS

| | | |
|---|---|---|
| WO | 2012133021 A1 | 10/2012 |
| WO | 2013117999 A1 | 8/2013 |

OTHER PUBLICATIONS

"Zeal Optics Revs Up Line with New Z3™ GPS Goggles", Published on: Sep. 22, 2011 Available at: http://www.prnewswire.com/news-releases/sports-latest-news/zeal-optics-revs-up-line-with-new-z3-gps-goggles-130342833.html.

(Continued)

*Primary Examiner* — Liliana Cerullo
(74) *Attorney, Agent, or Firm* — Alleman Hall Creasman & Tuttle LLP (57) ABSTRACT

A display system includes a display arranged in sight of a viewer, a sensory subsystem configured to sense an ocular condition of the viewer, and a controller. Operatively coupled to the display and to the sensory subsystem, the controller is configured to adjust an operating parameter of the display system in response to the ocular condition, in order to prevent or relieve eye discomfort experienced by the viewer.

15 Claims, 6 Drawing Sheets

(51) Int. Cl.
*A61B 3/113* (2006.01)
*A61B 3/14* (2006.01)

(56) References Cited

U.S. PATENT DOCUMENTS

| | | | |
|---|---|---|---|
| 8,549,415 B2 | 10/2013 | Tang | |
| 2002/0101506 A1* | 8/2002 | Suzuki | H04N 13/0207 348/51 |
| 2002/0122014 A1* | 9/2002 | Rajasingham | G02B 27/017 345/8 |
| 2005/0190180 A1 | 9/2005 | Jin et al. | |
| 2008/0062297 A1* | 3/2008 | Sako | G02B 27/017 348/333.02 |
| 2009/0115968 A1* | 5/2009 | Sugiyama | G02B 27/017 351/221 |
| 2012/0099195 A1 | 4/2012 | Choi et al. | |
| 2012/0250152 A1* | 10/2012 | Larson | G02B 27/2264 359/464 |
| 2013/0021373 A1 | 1/2013 | Vaught et al. | |
| 2013/0076878 A1 | 3/2013 | Nakajima | |
| 2013/0229711 A1 | 9/2013 | Kato et al. | |
| 2013/0241805 A1 | 9/2013 | Gomez | |
| 2013/0300635 A1 | 11/2013 | White et al. | |
| 2014/0002344 A1 | 1/2014 | Pai | |
| 2014/0361976 A1* | 12/2014 | Osman | G02B 27/0172 345/156 |
| 2015/0002373 A1* | 1/2015 | Kobayashi | G02B 27/017 345/8 |
| 2015/0029096 A1* | 1/2015 | Ishihara | H04N 5/63 345/156 |

OTHER PUBLICATIONS

"Sony revamps Personal 3D Viewer with HMZ-T2", Published on: Aug. 30, 2012 Available at: http://www.electronista.com/articles/12/08/30/sony.personal.3d.viewer.picks.up.welcome.revisions/.

"'Part Google Glass, Part Oculus Rift—parts Beat by Dre'—Meet Avegant Glyph", Published on: Dec. 18, 2013 Available at: http://www.futuristech.info/etc/part-google-glass-part-oculus-rift-parts-beat-by-dre-meet-avegant-glyph.

ISA European Patent Office, International Search Report and Written Opinion Issued in PCT Application No. PCT/US2015/050068, Jan. 5, 2016, WIPO, 15 pages.

IPEA European Patent Office, Second Written Opinion Issued in PCT Application No. PCT/US2015/050068, Aug. 5, 2016, WIPO, 11 pages.

IPEA European Patent Office, International Preliminary Report on Patentability Issued in PCT Application No. PCT/US2015/050068, Nov. 29, 2016, WIPO, 12 pages.

* cited by examiner

DISPLAY WITH EYE-DISCOMFORT REDUCTION

BACKGROUND

Modern display systems immerse the viewer in a convincing virtual reality. However, prolonged use of any display system may cause eye discomfort. Eye discomfort may arise simply from viewing display imagery (e.g., 3D stereo imagery) for an extended period of time. In some display systems, additional eye discomfort may be caused by probe light used to assess the viewer's identity, posture, or gaze direction.

SUMMARY

One embodiment provides a display system including a display arranged in sight of a viewer, a sensory subsystem configured to sense an ocular condition of the viewer, and a controller. Operatively coupled to the display and to the sensory subsystem, the controller is configured to adjust an operating parameter of the display system in response to the sensed ocular condition, in order to relieve eye discomfort that the viewer may be experiencing.

This summary is provided to introduce a selection of concepts in simplified form that are further described below in the detailed description. This summary is not intended to identify key features or essential features of the claimed subject matter, nor is it intended to limit the scope of the claimed subject matter. Furthermore, the claimed subject matter is not limited to implementations that solve any disadvantage noted in any part of this disclosure.

DETAILED DESCRIPTION

Aspects of this disclosure will now be described by example and with reference to the illustrated embodiments listed above. Components, process steps, and other elements that may be substantially the same in one or more embodiments are identified coordinately and described with minimal repetition. It will be noted, however, that elements identified coordinately may also differ to some degree. It will be further noted that the drawing figures included in this disclosure are schematic and generally not drawn to scale. Rather, the various drawing scales, aspect ratios, and numbers of components shown in the figures may be purposely distorted to make certain features or relationships easier to see.

Figure 1:
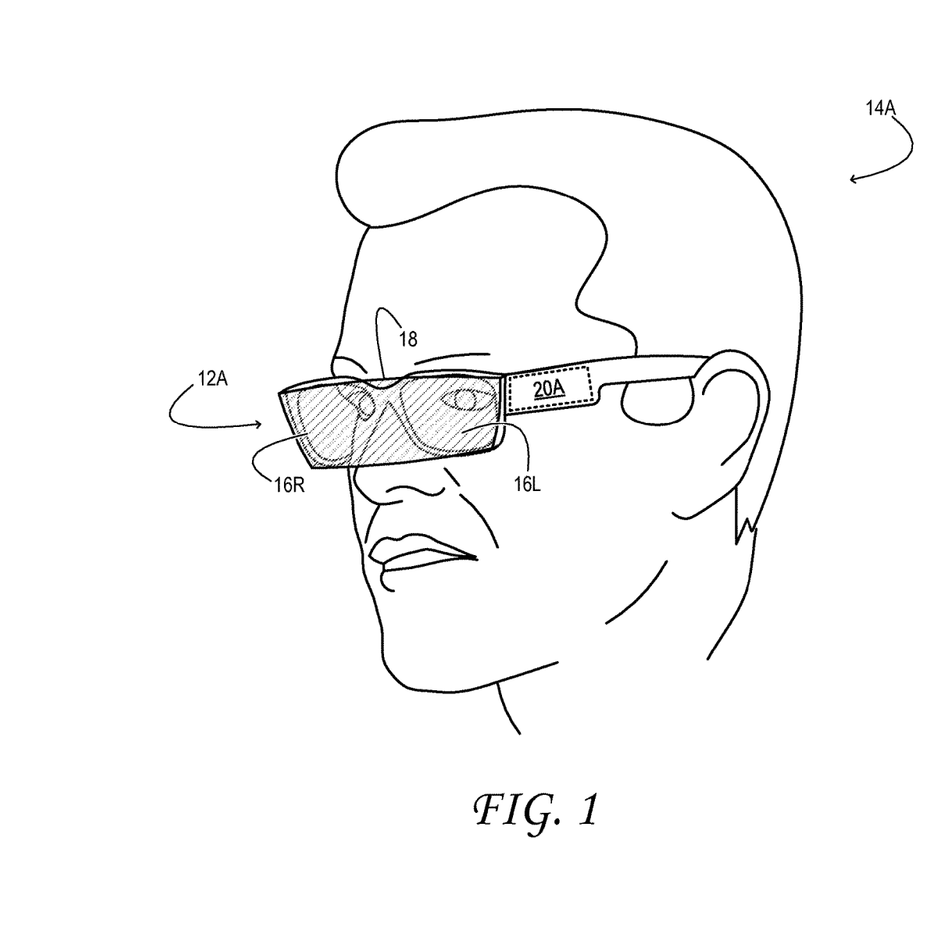
FIG. 1 shows aspects of an example head-mounted display system.

FIG. 1 shows aspects of an example head-mounted display system 12A to be worn and used by a wearer 14A. The illustrated display system includes stereoscopic, see-through display componentry positioned close to the wearer's eyes. Thus, display system 12A may be used in augmented-reality applications, where real-world imagery is admixed with virtual display imagery.

Display system 12A of FIG. 1 includes separate right and left display panels, 16R and 16L, and an electronically modulated dimming screen 18. In some embodiments, the right and left display panels are wholly or partly transparent from the perspective of the wearer, to give the wearer a clear view of his or her surroundings. Controller 20 is operatively coupled to the display panels, to the dimming screen, and to other display-system componentry. The controller includes logic and associated computer memory configured to enact the control processes described herein.

Figure 2:
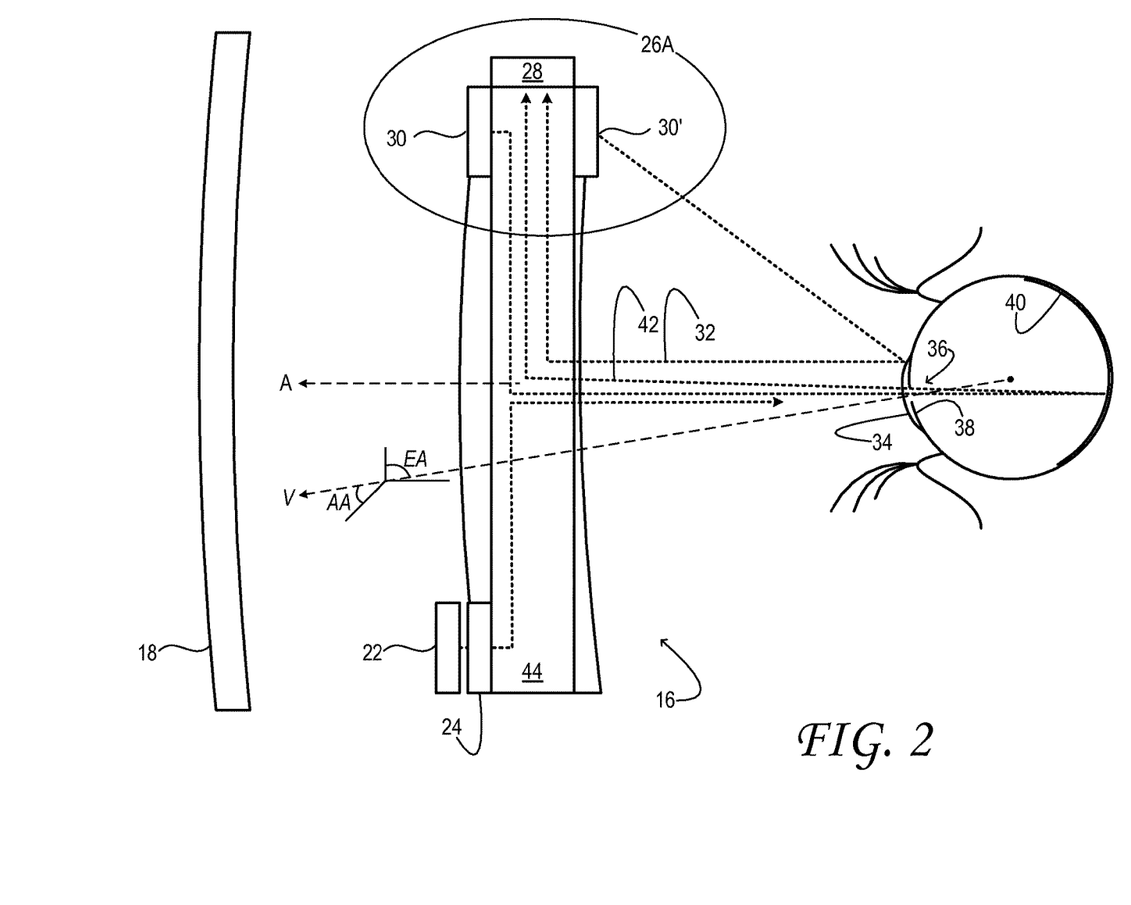
FIG. 2 shows aspects of an example display panel of a head-mounted display system.

FIG. 2 shows aspects of right or left display panel 16 (16R, 16L) in one, non-limiting embodiment. The display panel includes a backlight 22 and a liquid-crystal display (LCD) matrix 24. The backlight may include an ensemble of light-emitting diodes (LEDs)—e.g., white LEDs or a distribution of red, green, and blue LEDs. The backlight may be situated to direct its emission through the LCD matrix, which forms a display image based on control signals from controller 20A. The LCD matrix may include numerous, individually addressable pixels arranged on a rectangular grid or other geometry. In some embodiments, pixels transmitting red light may be juxtaposed in the matrix to pixels transmitting green and blue light, so that the LCD matrix forms a color image. In other embodiments, a reflective liquid-crystal-on-silicon (LCOS) matrix or a digital micromirror array may be used in lieu of the LCD matrix of FIG. 2. Alternatively, an active LED matrix or suitable scanned-beam technology may be used to form right and left display images. Although the drawings show separate right and left display panels, a single display panel extending over both eyes may be used instead.

Dimming screen 18 is configured to reduce, when needed, the brightness of real imagery viewed through display panel 16, so that virtual display imagery can be presented with adequate relative brightness. The dimming screen also reduces the wearer's exposure to ambient light—visible and otherwise. To this end, the dimming screen may include guest-host electrooptical technology, for example. In the illustrated embodiment, the dimming screen takes the form of a visor arranged over the right and left display panels. Accordingly, the dimming screen may be configured to controllably dim the wearer's entire field of view.

Head-mounted display system 12A includes a sensory subsystem 26A, also operatively coupled to controller 20A. In the illustrated embodiment, the sensory subsystem includes an eye-imaging camera 28, an on-axis illumination source 30 and an off-axis illumination source 30'. Each illumination source emits infrared (IR) or near-infrared (NIR) illumination in a high-sensitivity wavelength band of the eye-imaging camera. Each illumination source may comprise a light-emitting diode (LED), diode laser, discharge illumination source, etc. The terms 'on-axis' and 'off-axis' refer to the direction of illumination with respect to the optical axis A of the eye-imaging camera.

Through any suitable objective-lens system, eye-imaging camera 28 detects collects light over a range of field angles, mapping such angles to corresponding pixels of a rectangular pixel array. In one embodiment, the eye-imaging camera may detect the light in a plurality of wavelength channels—e.g., red, green, blue, etc.—associated with a subset of the pixels of the array. Alternatively, a monochromatic eye-imaging camera may be used, which images visible, near-infrared (NIR), infrared (IR), and/or ultraviolet (UV) light in grayscale. Color or brightness values for all of the pixels exposed in the eye-imaging camera constitute collectively a digital image. Controller 20A may be configured to use the output from the eye-imaging camera to track the gaze direction V of wearer 14A.

On- and off-axis illumination serve different purposes with respect to gaze tracking. As shown in FIG. 2, off-axis illumination can create a specular glint 32 that reflects from the cornea 34 of the wearer's eye. Off-axis illumination may also be used to illuminate the eye for a 'dark pupil' effect, where pupil 36 appears darker than the surrounding iris 38. By contrast, on-axis illumination from an IR or NIR source may be used to create a 'bright pupil' effect, where the pupil appears brighter than the surrounding iris. More specifically, IR or NIR illumination from on-axis illumination source 30 illuminates the retroreflective tissue of the retina 40 of the eye, which reflects the light back through the pupil, forming a bright image 42 of the pupil. Beam-turning optics 44 of display panel 16 enable the eye-imaging camera and the on-axis illumination source to share a common optical axis A, despite their arrangement on the periphery of the display panel. In some embodiments, the eye-imaging camera may include a wavelength filter blocking transmission outside of the emission band of the illumination sources, to improve bright-pupil contrast in the presence of strong ambient light.

Digital image data from eye-imaging camera 28 may be conveyed to associated logic in controller 20A or in a remote computer system accessible to the controller via a network. There, the image data may be processed to resolve such features as the pupil center, pupil outline, and/or one or more specular glints 32 from the cornea. The locations of such features in the image data may be used as input parameters in a model—e.g., a polynomial model—that relates feature position to the gaze vector V. In embodiments where a gaze vector is determined for the right and left eyes, the controller may also be configured to compute the wearer's focal point as the intersection of the right and left gaze vectors. In some embodiments, an eye-imaging camera may be used to enact an iris- or retinal-scan function to determine the identity of wearer 14A.

Prolonged use of head-mounted display system 12A may cause the wearer to experience eye discomfort or fatigue. Some eye discomfort may result simply from viewing display imagery from display panels 16 for a prolonged period of time. This type of discomfort may be muscular in nature—the result of keeping one's eyes open, repeated pupilary dilation and contraction, and/or rotation of the eye within its orbit. A wearer may also experience particular eye discomfort when viewing a stereo display—i.e., fatigue resulting from frequent accommodation changes to focus on virtual display imagery, and frustrated accommodation due to incorrect positioning of the head-mounted display system.

Additional eye discomfort may be caused by sensory-subsystem components of display system 12A. As noted above, illumination sources 30 and 30' may emit IR or NIR probe light to illuminate eye for imaging purposes. Light of such wavelengths may heat the eye, causing evaporation of surface liquid and a feeling of dryness. Moreover, some individuals may have an abnormal sensitivity in the NIR, experiencing eye discomfort due to prolonged exposure to NIR probe light.

Figure 3:
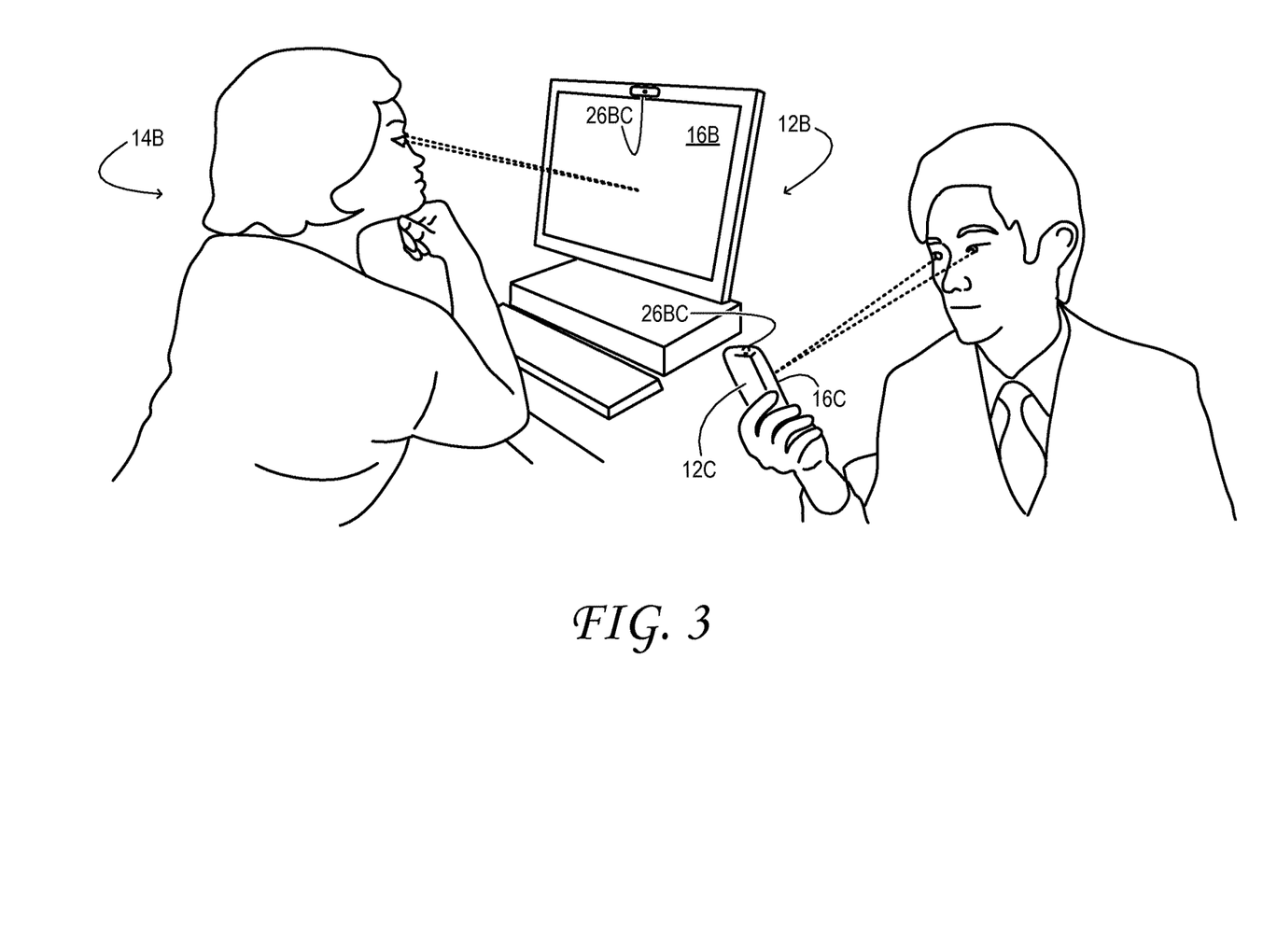
FIGS. 3 and 4 show aspects of other example display systems.

The foregoing drawings and description identify one example display system 12A and associated eye-discomfort issues. Other, quite different, display systems also lie within the spirit and scope of this disclosure. FIG. 3 shows display systems 12B and 12C, which are neither head-mounted nor wearable. Display system 12B is a desktop computer system. In lieu of near-eye display panels 16R and 16L, display system 12B includes a computer monitor 16B arranged in sight of viewer 14B. Display system 12C is a smart phone or tablet having a touch-screen display 16C. In the embodiments of FIG. 3, a sensory subsystem 26BC including an eye-imaging camera is arranged beneath the bezel of each display. The displays shown in FIG. 3 are not necessarily stereoscopic; nevertheless, prolonged viewing of the display and/or exposure to probe light from sensory subsystem may cause the viewer to experience eye discomfort.

Figure 4:
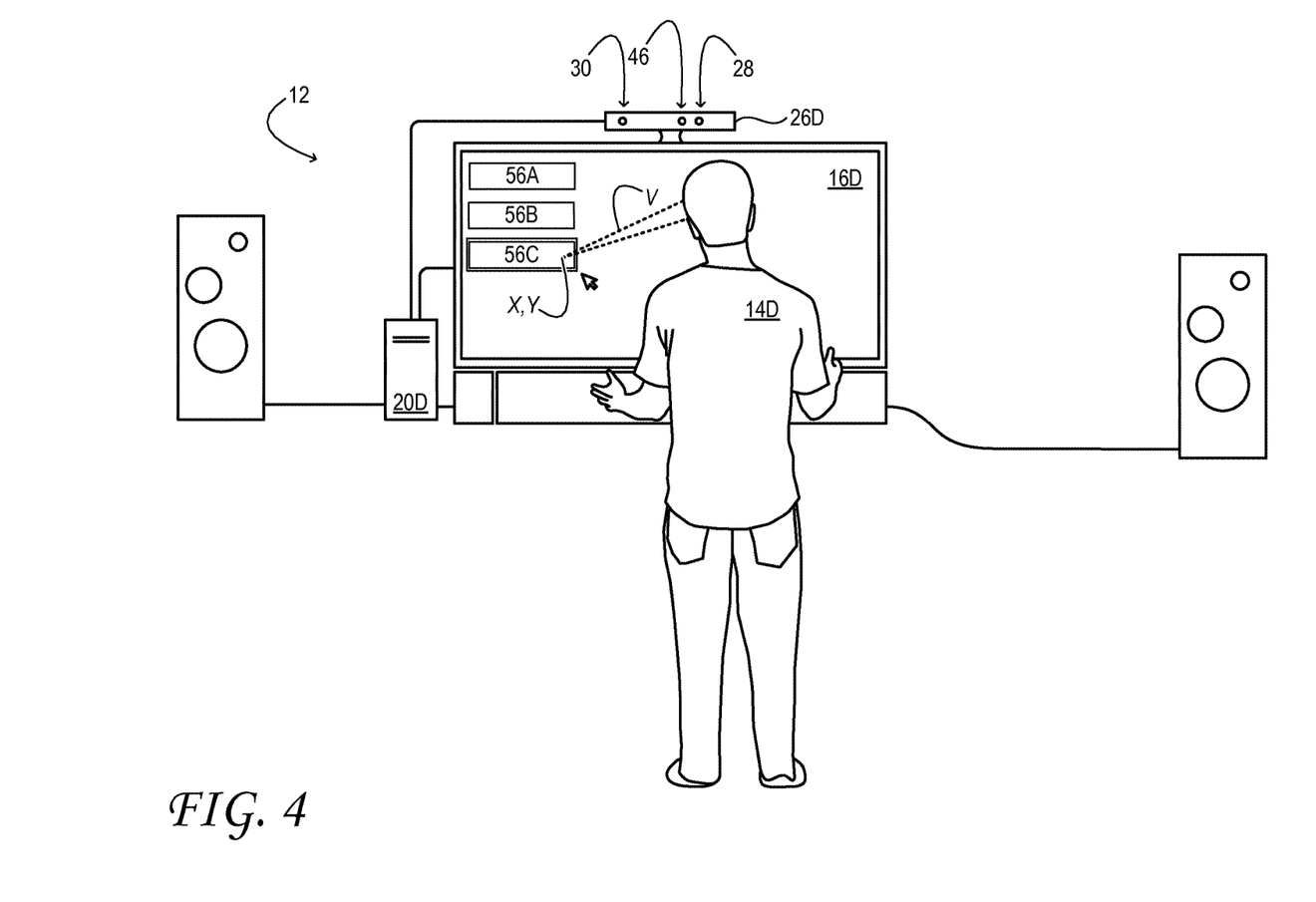

FIG. 4 shows yet another embodiment of a display system, in the form of home-entertainment system 12D. This system may also function as a game system, multimedia system, or productivity system. It includes a large format display 16D and a sensory subsystem 26D peripheral to the display. In this embodiment, controller 20D may take the form of a PC or game system operatively coupled to the display and to the sensory subsystem. In the embodiment of FIG. 4, the sensory subsystem takes the form of a vision system with a flat-image camera 28 and a depth camera 46 for gesture detection. An IR or NIR illumination source 30D provides illumination of viewer 14D for eye tracking and/or depth imaging. In some embodiments, sensory subsystem 26D may include dedicated on- and off-axis illumination sources, as described hereinabove.

Depth camera 46 may be configured to acquire a time-resolved sequence of depth maps of viewer 14D and aspects of the viewer's environment. As used herein, the term 'depth map' refers to an array of pixels registered to corresponding regions $(X_i, Y_i)$ of an imaged scene, with a depth value $Z_i$ indicating, for each pixel, the depth of the corresponding region. 'Depth' may be defined as a coordinate parallel to the optical axis of the depth camera, which increases with increasing distance from the depth camera.

In general, the nature of depth camera 46 may differ in the various embodiments of this disclosure. In one embodiment, brightness or color data from two, stereoscopically oriented imaging arrays in a depth camera may be co-registered and used to construct a depth map. In other embodiments, illumination source 30 may be configured to project onto the subject a structured infrared (IR) illumination pattern comprising numerous discrete features—e.g., lines or dots. An imaging array in the depth camera may be configured to image the structured illumination reflected back from the subject. Based on the spacings between adjacent features in the various regions of the imaged subject, a depth map of the subject may be constructed. In still other embodiments, a depth camera may project a pulsed infrared illumination towards the subject. A pair of imaging arrays in the depth camera may be configured to detect the pulsed illumination reflected back from the subject. Both arrays may include an electronic shutter synchronized to the pulsed illumination, but the integration times for the arrays may differ, such that a pixel-resolved time-of-flight of the pulsed illumination, from the illumination source to the subject and then to the arrays, is discernible based on the relative amounts of light received in corresponding elements of the two arrays.

Controller 20D—and indeed any of the controllers described herein—may include various functional processing engines instantiated in software and/or firmware. This aspect is further illustrated in FIG. 5. A gesture-recognition engine 48 in controller 20D may be configured to process the depth data from depth camera 46, to identify one or more human subjects in the depth data, to compute various skeletal features of the subjects identified, and to gather from the skeletal features various postural or gestural information, which is furnished to OS 50 or to application 52 executing on the controller.

In the scenario illustrated in FIG. 4, for example, viewer 14D is navigating a UI presented on display 16D based on gaze direction or hand gesture. In one example, a gaze-tracking engine 54 in controller 20D computes display screen coordinates (X, Y) corresponding to the point that the user is gazing at, based on image data from flat-image camera 28D. By shifting his gaze to other points on the display screen, the viewer can navigate among the various UI elements 56 presented on the display. Alternatively, or in addition, gesture-recognition engine 48 may be configured to compute UI coordinates based on the position of the viewer's hand relative to a coordinate system fixed to the viewer's body. In this and other embodiments, face-recognition engine 58 of the controller may be configured to process image data from one or more cameras of the sensory subsystem, to analyze the facial features of the current viewer. Analysis of the facial features may enable the current viewer to be identified—e.g., matched to a profile stored in the controller or in a networked computer system.

Though several, distinct display-system embodiments are described herein, this disclosure also embraces any appropriate subcombination of features from the various embodiments. A tablet or smartphone, for instance, may include a sensory subsystem equipped for depth imaging and gesture detection. A home-entertainment system may include a large-format stereoscopic display. Numerous other subcombinations are envisaged as well.

To address the eye-discomfort issues noted above, controller 20 (20A, 20B, etc.) may be configured to adjust one or more operating parameters of display system 12 (12A, 12B, etc.) in response to an ocular condition of a viewer of the display system—i.e., a condition that indicates current or impending eye discomfort. Operating parameters are adjusted in order to prevent or relieve the viewer's discomfort, returning the viewer to a comfortable state.

To this end, and turning again to FIG. 5, sensory subsystem 26 (26A, 26B, etc.) may include an ocular sensor 60 configured to sense an ocular condition of viewer 14. In some embodiments, the ocular sensor may be responsive to eye stress. The ocular sensor may be a non-contact eye-temperature sensor, for example, which senses eye heating and/or fluid evaporation due to IR or NIR illumination of the viewer's eye. In other examples, the ocular sensor may be an imaging sensor configured to image the viewer's eye. An ocular sensor of this kind may be configured to sense eye redness, dilated capillaries, or partial closure of the eyelid. In these and other embodiments, the imaging ocular sensor may be configured to sense pupil dilation. The imaging ocular sensor may take the form of a digital camera—e.g., a web camera, IR-enabled web camera, or, a web camera equipped with a long-wavelength IR sensor responsive to the surface temperature of the imaged eye. In more particular examples, the imaging ocular sensor may be capable of resolving eye-irritating atmospheric particulates in the viewer's eye. In some embodiments, ocular sensor 60 may be configured to sense various kinds of eye movement: relatively slow rotation of the eye in its orbit, corresponding to changes in the viewer's gaze direction; faster, saccadic rotation of the eye; and very rapid eye movement associated with twitch.

In some scenarios, output from ocular sensor 60 may indicate that the viewer is experiencing eye discomfort, or that eye discomfort is likely to occur in the short term. For example, eye discomfort may be indicated by increased temperature at the surface of the eye, by increased redness or dilated capillaries, by increased closure of the eyelid, or by the presence of particulates in the viewer's eye. Indicators such as these report directly on eye stress. However, less direct indicators of eye stress may also be used. For example, eye discomfort may be indicated based on the frequency of change in pupilary size (discomfort increasing with increasing frequency), and on the frequency with which the viewer's focal point is shifted. Discomfort may be preceded by frequent shifting of the focal point to focal planes situated at different depths, as well as horizontal and vertical shifting within a given focal plane.

As noted above, if a sensed ocular condition is indicative of current or impending eye discomfort, controller 20 may proactively adjust one or more operating parameters of display system 12 to relieve or prevent the discomfort. The operating parameter chosen for adjustment may differ in the different embodiments of this disclosure, and in different operating scenarios of the same embodiment.

In some implementations, the operating parameter subject to adjustment may be a parameter of display 16 (16A, 16B, etc.). For example, display-image brightness may be adjusted (viz., reduced) when eye discomfort is sensed or predicted. Since the human eye is more sensitive to green light than to any other color, intensity in the red and especially the blue channel of an RGB display may be reduced while preserving intensity in the green channel. This approach may be used to relieve eye discomfort in cases where further reduction in overall intensity would compromise display-image visibility.

Another operating parameter of display 16 that can be adjusted to relieve discomfort is the display-image hue. Cooler colors tend to be imaged less sharply on the human retina than warmer colors, causing more frequent accommodation attempts and increased eye fatigue. Thus, the display-image hue may be warmed (e.g., reddened) when eye discomfort is sensed or predicted. The display-image frame rate may also be adjusted to relieve eye discomfort. In particular, lower frame rates may be used when eye discomfort is detected, to trigger less frequent shifting of the focal-point. If display 16 is equipped with a dimming screen 18, the opacity of the dimming screen may be increased to reduce eye discomfort caused by ambient light and/or real imagery. In stereoscopic display systems, the display-image depth may also be adjusted. In particular, horizontal disparity between right and left image frames may be reduced, thereby flattening the display image when eye discomfort is sensed. This action frees the ocular cortex of the need to 'fuse' the right and left images, which may relieve or prevent eye discomfort.

In other embodiments, the operating parameter subject to adjustment may be a parameter of sensory subsystem 26. For example, illumination intensity of an IR illumination source directed toward the viewer may be reduced, as needed, to relieve eye discomfort. In light-emitting diode based illumination sources, the modulation (i.e., duty cycle) may be adjusted in lieu of or in addition to the intensity.

Figure 5:
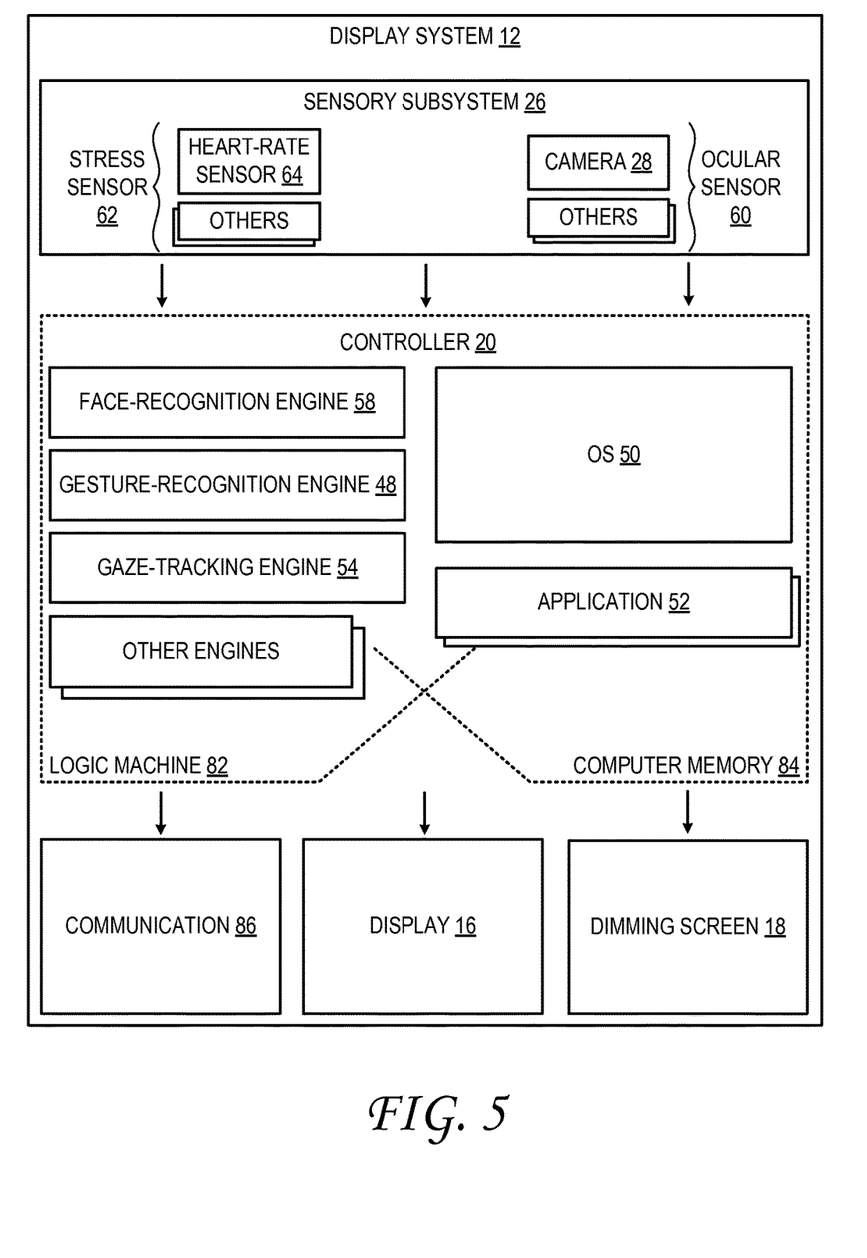
FIG. 5 shows additional aspects of an example display system.

The embodiments described above emphasize direct assessment of an ocular condition of viewer 14 to determine whether to adjust an operating parameter of display system 12. Other embodiments assess the ocular condition in combination with at least one indication of physiological stress. Accordingly, sensory subsystem 26 may include, in addition to ocular sensor 60, at least one stress sensor 62 configured to sense physiological stress on the viewer. Stress may be sensed directly or indirectly. The stress sensors here contemplated may include a heart-rate sensor 64, a respiration sensor, a blood-pressure sensor, a heart-waveform sensor, a blood-sugar sensor, a blood-oxygen sensor, an ambient carbon-dioxide sensor, a perspiration sensor based on skinresistance measurement, and/or a skin-temperature sensor, as non-limiting examples. Controller 20 may be configured to estimate actual or predicted eye discomfort based on the ocular condition as reported by the ocular sensor, combined with physiological stress as reported by the stress sensor. In some embodiments, a fuzzy-logic approach may be used to provide the estimate.

In one example, transient increased heart rate with concurrent eye movement or change in pupillary size may indicate that the viewer is experiencing eye discomfort. Suitable surrogates for increased heart rate in the above example may include increased respiration, increased blood pressure, abnormal heart waveforms, transiently high or low blood sugar, transiently low blood oxygenation, increased ambient carbon dioxide levels, or increased skin temperature or perspiration.

The foregoing description should not be understood in a limiting sense, for numerous variations and extensions are contemplated as well. For example, controller 20 may be configured to adjust an operating parameter of display system 12, as described above, but in view of a performance constraint in the display system. When display 16 is being used to display text, for example, significant reduction in display-image brightness or adjustment of hue may be tolerable—or even appreciated—by a viewer experiencing eye discomfort. Likewise, if gaze vectors are used only to navigate a user interface, the uncomfortable viewer may be willing to tolerate less accurate gaze tracking. Under such conditions, aggressive adjustment of the operating parameter—reduction of display-image brightness or probe illumination—may be appropriate. On the other hand, if the user is immersed in graphics-intensive gaming, where survival depends on accurate gaze tracking and ability to resolve details in a virtual environment, then any reduction in display-system performance may be unwelcome, even for the sake of comfort. In another example, display-image brightness may be reduced more under darker ambient conditions, in response to eye discomfort, than under brighter ambient conditions. In another example, eye discomfort under darker ambient conditions may trigger reduction of the display-image brightness, while the same discomfort under brighter ambient conditions may trigger activation of dimming screen 18, with less reduction in display-image brightness.

Although the drawings herein show a fully integrated sensory subsystem 26, this aspect is by no means necessary. In some embodiments, the sensory subsystem may include one or more remote sensors—i.e., sensors not physically coupled to the display. Such sensors may be incorporated in an intelligent wrist band or handheld device, for example, communicatively coupled to controller 20 via a wireless network.

The configurations described above enable various methods to prevent or relieve eye discomfort that may be experienced by a viewer of a display system. One such method is now described with continued reference to the example configurations described above. It will be understood, however, that the methods here described, and others within the scope of this disclosure, also may be enabled by different configurations.

Figure 6:
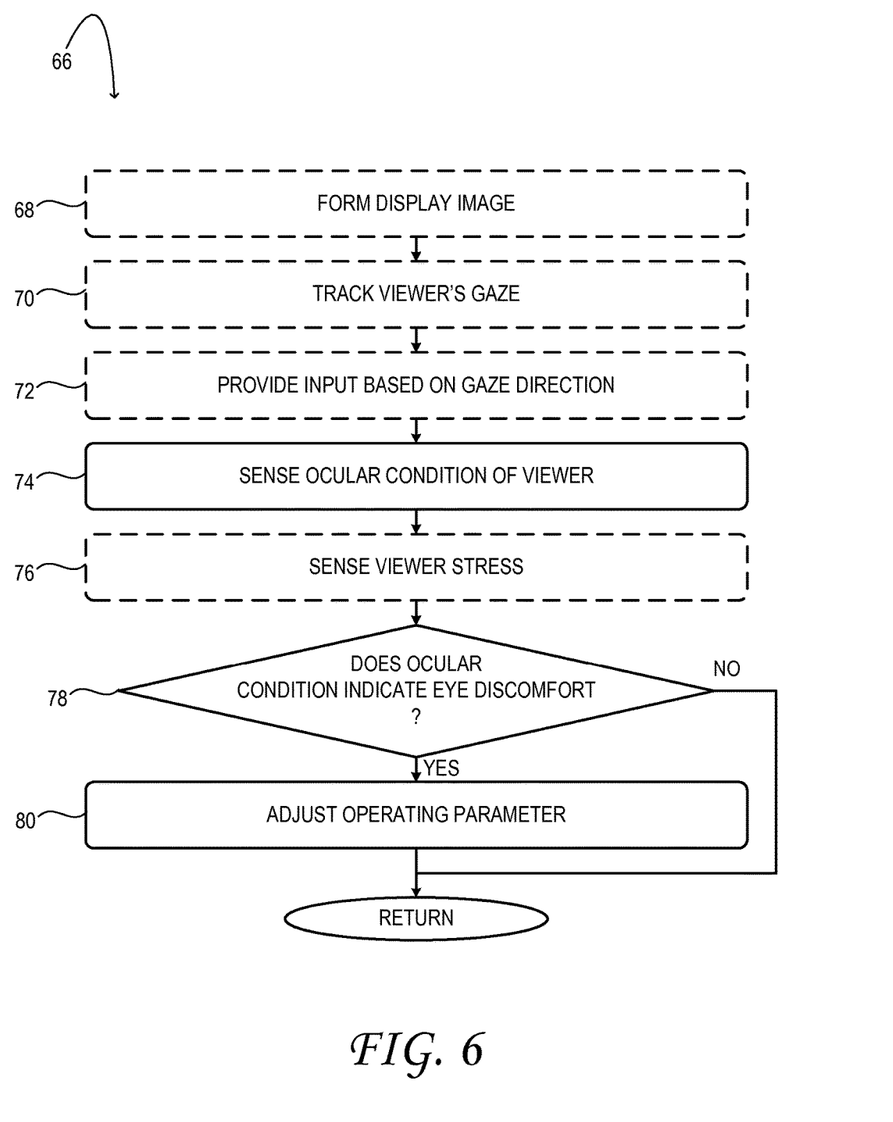
FIG. 6 illustrates an example method to relieve or prevent eye discomfort for a viewer of a display system.

FIG. 6 illustrates an example method 66 to prevent or relieve eye discomfort that may be experienced by a viewer of a display system. At 68 of method 66, a display image is formed in associated display componentry of the display system. At 70, the viewer's gaze direction is tracked via a sensory subsystem of the display system. At 72, user input is provided in the display system based on the tracked gaze direction.

At 74, an ocular condition of the viewer is sensed via the sensory subsystem. At optional step 76, at least one additional indicator of viewer stress is sensed. At 78, it is determined whether the sensed ocular condition indicates that the viewer is experiencing eye discomfort, or that eye discomfort is likely to occur. In a more particular example, the determination at 78 may be further based on the at least one additional indicator of viewer stress from 76. If it is determined that the viewer is experiencing (or is likely to experience) eye discomfort, then at 80, an operating parameter of the display system is adjusted to prevent or relieve the eye discomfort.

As evident from the foregoing description, the methods and processes described herein may be tied to a computer system of one or more computing machines. Such methods and processes may be implemented as a computer-application program or service, an application-programming interface (API), a library, and/or other computer-program product. FIG. 5 shows a non-limiting example of a computer system in the form of controller 20, which supports the methods and processes described herein. The computer system includes a logic machine 82 and associated computer memory 84.

Logic machine 82 includes one or more physical logic devices configured to execute instructions. A logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 82 may include one or more processors configured to execute software instructions. Additionally or alternatively, a logic machine may include one or more hardware or firmware logic machines configured to execute hardware or firmware instructions. Processors of a logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices configured in a cloud-computing configuration.

Computer memory 84 includes one or more physical, computer-memory devices configured to hold instructions executable by the associated logic machine 82 to implement the methods and processes described herein. When such methods and processes are implemented, the state of the computer memory may be transformed—e.g., to hold different data. Computer memory may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Computer memory may include volatile, nonvolatile, dynamic, static, read/write, read-only, random-access, sequential-access, location-addressable, file-addressable, and/or content-addressable devices.

It will be appreciated that computer memory 84 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 82 and computer memory 84 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term 'engine' may be used to describe an aspect of a computer system implemented to perform a particular function. In some cases, an engine may be instantiated via a logic machine executing instructions held in computer memory. It will be understood that different engines may be instantiated from the same application, service, code block, object, library, routine, API, function, etc. Likewise, the same engine may be instantiated by different applications, services, code blocks, objects, routines, APIs, functions, etc. The term 'engine' may encompass individual or groups of executable files, data files, libraries, drivers, scripts, database records, etc.

Communication system 124 may be configured to communicatively couple the computer system to one or more other machines. The communication system may include wired and/or wireless communication devices compatible with one or more different communication protocols. As non-limiting examples, a communication system may be configured for communication via a wireless telephone network, or a wired or wireless local- or wide-area network. In some embodiments, a communication system may allow a computing machine to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A near-eye display system comprising:
a display portion arranged in sight of a viewer;
an arrangement of sensor elements configured to sense infrared light from the eye, the arrangement of sensor elements including a plurality of imaging sensor elements of an eye-imaging camera;
one or more infrared light sources configured to illuminate the eye, the one or more infrared light sources providing the infrared light sensed by the imaging sensor elements; and
an electronic controller operatively coupled to the arrangement of sensor elements and to the one or more infrared light sources, and configured to assess at least one of eye heating and fluid evaporation experienced by the viewer by interrogating the arrangement of sensor elements, the controller being further configured to track a gaze direction of the viewer by interrogating the plurality of imaging sensor elements, and to adjust illumination intensity of the one or more infrared light sources responsive to output from the arrangement of sensor elements, so as to reduce the at least one of eye heating and fluid evaporation as assessed by the controller.

2. The display system of claim 1, wherein the controller is further configured to adjust a parameter of the display portion in response to the at least one of eye heating and fluid evaporation, so as to reduce the at least one of eye heating and fluid evaporation as assessed by the controller.

3. The display system of claim 2, wherein the parameter of the display portion includes display-image brightness.

4. The display system of claim 2, wherein the parameter of the display portion includes display-image depth.

5. The display system of claim 1, wherein the plurality of imaging sensor elements are configured to sense eye movement.

6. The display system of claim 1, wherein the plurality of imaging sensor elements are configured to sense pupil dilation.

7. The display system of claim 1, wherein the arrangement of sensor elements is configured to sense one or more of increased heat rate, increased respiration, increased blood pressure, abnormal heart waveform, transient low blood sugar, low blood oxygenation, increased carbon dioxide level, increased skin temperature, and increased perspiration of the viewer.

8. The display system of claim 1, wherein the arrangement of sensor elements includes a non-contact eye-temperature sensor so as to be responsive to the at least one of eye heating and fluid evaporation.

9. The display system of claim 1, wherein the sensory subsystem includes one or more remote sensors.

10. The display system of claim 1, wherein the controller is configured to adjust the illumination intensity of the one or more infrared light sources subject to a performance constraint of the display system.

11. A wearable, head-mounted display system comprising:
a stereoscopic, see-through display portion positioned close to a wearer's eye;
an arrangement of sensor elements configured to sense infrared light from the eye, the arrangement of sensor elements including a plurality of imaging sensor elements of an eye-imaging camera;
one or more infrared light sources configured to illuminate the eye, the one or more infrared light sources providing the infrared light sensed by the imaging sensor elements; and
an electronic controller operatively coupled to the arrangement of sensor elements and to the one or more infrared light sources, and configured to assess at least one of eye heating and fluid evaporation experienced by the viewer by interrogating the arrangement of sensor elements, the controller being further configured to track a gaze direction of the viewer by interrogating the plurality of imaging sensor elements, and to adjust illumination intensity of the one or more infrared light sources responsive to output from the arrangement of sensor elements, so as to reduce the at least one of eye heating and fluid evaporation as assessed by the controller.

12. The head-mounted display system of claim 11, wherein the stereoscopic, see-through display portion includes an electronically modulated diming screen configured to controllably reduce transmission of ambient light and real-world imagery to the wearer's eye, and wherein the controller is further configured to adjust opacity of the dimming screen.

13. A display system comprising:
a display portion arranged in sight of a viewer;
an arrangement of sensor elements configured to sense infrared light from the eye, the arrangement of sensor elements including a plurality of imaging sensor elements of an eye-imaging camera;
one or more infrared light sources configured to illuminate the eye, the one or more infrared light sources providing the infrared light sensed by the imaging sensor elements
an additional stress sensor configured to detect one or more of increased heat rate, increased respiration, increased blood pressure, abnormal heart waveform, transient low blood sugar, low blood oxygenation, increased carbon dioxide level, increased skin temperature, and increased perspiration of the viewer; and
an electronic controller operatively coupled to the arrangement of sensor elements, to the additional stress sensor, and to the one or more infrared light sources, and configured to assess at least one of eye heating and fluid evaporation experienced by the viewer by interrogating the arrangement of sensor elements and additional stress sensor, the controller being further configured to track a gaze direction of the viewer by interrogating the plurality of imaging sensor elements, and to adjust illumination intensity of the one or more infrared light sources responsive to output from the arrangement of sensor elements and additional stress sensor, so as to reduce the at least one of eye heating and fluid evaporation as assessed by the controller.

14. The display system of claim 13, wherein the additional stress sensor is one or more of a heart-rate sensor, respiration sensor, blood-pressure sensor, heart waveform sensor, blood-sugar sensor, blood-oxygen sensor, ambient carbon-dioxide sensor, perspiration sensor and skin-temperature sensor.

15. The display system of claim 13, wherein the controller is configured to assess the at least one of eye heating and fluid evaporation based on the output from the arrangement of sensor elements combined with the one or more of increased heat rate, increased respiration, increased blood pressure, abnormal heart waveform, transient low blood sugar, low blood oxygenation, increased carbon dioxide level, increased skin temperature, and increased perspiration reported by the additional stress sensor.

* * * * *